US012616564B2

(12) United States Patent
Nguyen et al.

(10) Patent No.: US 12,616,564 B2
(45) Date of Patent: May 5, 2026

(54) BRANCH ENDOPROSTHETIC SYSTEMS, DEVICES, AND METHOD

(71) Applicant: W. L. Gore & Associates, Inc., Newark, DE (US)

(72) Inventors: Minh Nguyen, Flagstaff, AZ (US); Timothy J. O'Neill, Flagstaff, AZ (US); Aniceto Trujillo, Flagstaff, AZ (US)

(73) Assignee: W. L. Gore & Associates. Inc., Newark, DE (US)

( * ) Notice: Subject to any disclaimer, the term of this patent is extended or adjusted under 35 U.S.C. 154(b) by 695 days.

(21) Appl. No.: 17/798,138

(22) PCT Filed: Feb. 7, 2020

(86) PCT No.: PCT/US2020/017219
§ 371 (c)(1),
(2) Date: Aug. 8, 2022

(87) PCT Pub. No.: WO2021/158234
PCT Pub. Date: Aug. 12, 2021

(65) Prior Publication Data
US 2023/0070265 A1 Mar. 9, 2023

(51) Int. Cl.
*A61F 2/07* (2013.01)
*A61F 2/06* (2013.01)

(52) U.S. Cl.
CPC .................. *A61F 2/07* (2013.01); *A61F 2/06* (2013.01); *A61F 2240/001* (2013.01)

(58) Field of Classification Search
CPC ........ A61F 2/07; A61F 2/06; A61F 2002/065; A61F 2240/001; A61F 2002/072
See application file for complete search history.

(56) References Cited

U.S. PATENT DOCUMENTS 3,953,566 A 4/1976 Gore
4,187,390 A 2/1980 Gore
(Continued)

FOREIGN PATENT DOCUMENTS

CN 103932820 A 7/2014
CN 104363858 A 2/2015
(Continued)

OTHER PUBLICATIONS

International Preliminary Report on Patentability received for PCT Patent Application No. PCT/US2020/017219, mailed on Aug. 18, 2022, 12 pages.
(Continued)

*Primary Examiner* — Monica A Huson

(57) ABSTRACT

Bifurcated endoprosthetic devices, systems and methods are disclosed herein for treating disease of human vasculature. In various embodiments, a bifurcated endoprosthesis includes a trunk portion and a plurality of legs, where the legs are constrained such that they maintain alignment with one another. In some examples, the legs and bifurcation of an endoprosthetic device may be formed by cutting a tubular graft component along a portion of less than its entire circumference in a longitudinally central region, and then folding the tubular graft component along the uncut portion to define two legs, where the uncut portion defines the bifurcation. In some such examples, the folded tubular graft component can be coupled with a tubular trunk component to form the bifurcated endoprosthetic device.

23 Claims, 12 Drawing Sheets

(56) References Cited

U.S. PATENT DOCUMENTS

| | | | |
|---|---|---|---|
| 4,503,569 A | 3/1985 | Dotter |
| 4,512,338 A | 4/1985 | Balko et al. |
| 4,990,155 A | 2/1991 | Wilkoff |
| 5,037,427 A | 8/1991 | Harada et al. |
| 5,147,370 A | 9/1992 | McNamara et al. |
| 5,211,658 A | 5/1993 | Clouse |
| 5,221,261 A | 6/1993 | Termin et al. |
| 5,276,276 A | 1/1994 | Gunn |
| 5,755,735 A | 5/1998 | Richter et al. |
| 5,922,019 A | 7/1999 | Hankh et al. |
| 6,042,602 A | 3/2000 | Wells |
| 6,086,610 A | 7/2000 | Duerig et al. |
| 6,102,940 A | 8/2000 | Robichon et al. |
| 6,110,198 A | 8/2000 | Fogarty et al. |
| 6,120,534 A | 9/2000 | Ruiz |
| 6,139,573 A | 10/2000 | Sogard et al. |
| 6,203,735 B1 | 3/2001 | Edwin et al. |
| 6,210,429 B1 | 4/2001 | Vardi et al. |
| 6,327,772 B1 | 12/2001 | Zadno-Azizi et al. |
| 6,336,937 B1 | 1/2002 | Vonesh et al. |
| 6,352,561 B1 | 3/2002 | Leopold et al. |
| 6,355,057 B1 | 3/2002 | Demarais et al. |
| 6,366,937 B1 | 4/2002 | Shridhar et al. |
| 6,395,212 B1 | 5/2002 | Solem |
| 6,402,779 B1 | 6/2002 | Colone et al. |
| 6,551,350 B1 | 4/2003 | Thornton et al. |
| 6,613,077 B2 | 9/2003 | Gilligan et al. |
| 6,635,083 B1 | 10/2003 | Cheng et al. |
| 6,729,356 B1 | 5/2004 | Baker et al. |
| 6,773,454 B2 | 8/2004 | Wholey et al. |
| 6,899,727 B2 | 5/2005 | Armstrong et al. |
| 6,981,982 B2 | 1/2006 | Armstrong et al. |
| 7,049,380 B1 | 5/2006 | Chang et al. |
| 7,731,744 B1 | 6/2010 | Cox |
| 8,021,413 B2 | 9/2011 | Dierking et al. |
| 8,048,138 B2 | 11/2011 | Sullivan et al. |
| 8,177,927 B2 | 5/2012 | Dooley et al. |
| 8,257,431 B2 | 9/2012 | Henderson et al. |
| 8,702,791 B2 | 4/2014 | Kelly |
| 8,945,200 B1 | 2/2015 | Eblacas et al. |
| 11,376,112 B2 | 7/2022 | Silverman et al. |
| 11,786,356 B2 | 10/2023 | Buckley et al. |
| 2001/0039446 A1 | 11/2001 | Edwin et al. |
| 2001/0049550 A1 | 12/2001 | Martin et al. |
| 2001/0053929 A1 | 12/2001 | Vonesh et al. |
| 2002/0007210 A1 | 1/2002 | Chouinard et al. |
| 2002/0007955 A1 | 1/2002 | Wiens |
| 2002/0177891 A1 | 11/2002 | Parodi |
| 2004/0063805 A1 | 4/2004 | Pacetti et al. |
| 2005/0049667 A1 | 3/2005 | Arbefeuille et al. |
| 2005/0129732 A1 | 6/2005 | Rubsamen |
| 2005/0234542 A1 | 10/2005 | Melsheimer |
| 2006/0052865 A1 | 3/2006 | Banas |
| 2006/0198866 A1 | 9/2006 | Chang et al. |
| 2007/0250153 A1 | 10/2007 | Cully et al. |
| 2008/0039927 A1 | 2/2008 | Barr |
| 2008/0071356 A1 | 3/2008 | Greenhalgh et al. |
| 2008/0103587 A1 | 5/2008 | Henderson et al. |
| 2008/0288044 A1 | 11/2008 | Osborne |
| 2009/0048662 A1 | 2/2009 | Pavcnik et al. |
| 2010/0280592 A1 | 11/2010 | Shin et al. |
| 2012/0323304 A1 | 12/2012 | Buckley et al. |
| 2013/0131780 A1 | 5/2013 | Armstrong et al. |
| 2013/0274861 A1 | 10/2013 | Kelly |
| 2014/0120287 A1 | 5/2014 | Jacoby et al. |
| 2015/0005870 A1 | 1/2015 | Kovach et al. |
| 2015/0081007 A1 | 3/2015 | Joye et al. |
| 2015/0282959 A1 | 10/2015 | Dunn |
| 2016/0177422 A1 | 6/2016 | Schaffer |
| 2017/0196715 A1 | 7/2017 | Joye et al. |
| 2019/0388214 A1 | 12/2019 | Silverman et al. |
| 2020/0289254 A1 | 9/2020 | Buckley et al. |
| 2022/0331090 A1 | 10/2022 | Silverman et al. |
| 2023/0414341 A1 | 12/2023 | Buckley et al. |

FOREIGN PATENT DOCUMENTS

| | | |
|---|---|---|
| CN | 104379090 A | 2/2015 |
| CN | 105744913 A | 7/2016 |
| CN | 205411404 U | 8/2016 |
| EP | 0866678 B1 | 9/2007 |
| JP | 11-509130 A | 8/1999 |
| JP | 2002-531219 A | 9/2002 |
| JP | 2003-505144 A | 2/2003 |
| JP | 2003-521313 A | 7/2003 |
| JP | 2005-514968 A | 5/2005 |
| JP | 2007-503923 A | 3/2007 |
| JP | 2012-506956 A | 3/2012 |
| JP | 2014-058710 A | 4/2014 |
| JP | 2015-512755 A | 4/2015 |
| JP | 2016-530065 A | 9/2016 |
| JP | 2017-509439 A | 4/2017 |
| JP | 2023-513212 A | 3/2023 |
| WO | 97/21403 A1 | 6/1997 |
| WO | 97/33532 A2 | 9/1997 |
| WO | 98/26731 A2 | 6/1998 |
| WO | 00/33770 A2 | 6/2000 |
| WO | 01/06953 A1 | 2/2001 |
| WO | 01/24733 A1 | 4/2001 |
| WO | 2002/100297 A2 | 12/2002 |
| WO | 2010/051515 A1 | 5/2010 |
| WO | 2013/155306 A1 | 10/2013 |
| WO | 2013/155309 A2 | 10/2013 |
| WO | 2013/155311 A1 | 10/2013 |
| WO | 2021/158234 A1 | 8/2021 |

OTHER PUBLICATIONS

International Search Report and Written Opinion received for PCT Patent Application No. PCT/US2020/017219, mailed on Oct. 23, 2020, 15 pages.

Blandford, R. K., Blandford et al., "Tensile Stress-Strain Results for 304L and 316L Stainless Steel Plate at Temperature", ASME, 2007, pp. 617-628., Jul. 20, 2007.

Blandford et al., "Tensile Stress-Strain Results for 304L and 316L Stainless Steel Plate at Temperature", ASME, 2009, pp. 617-628.

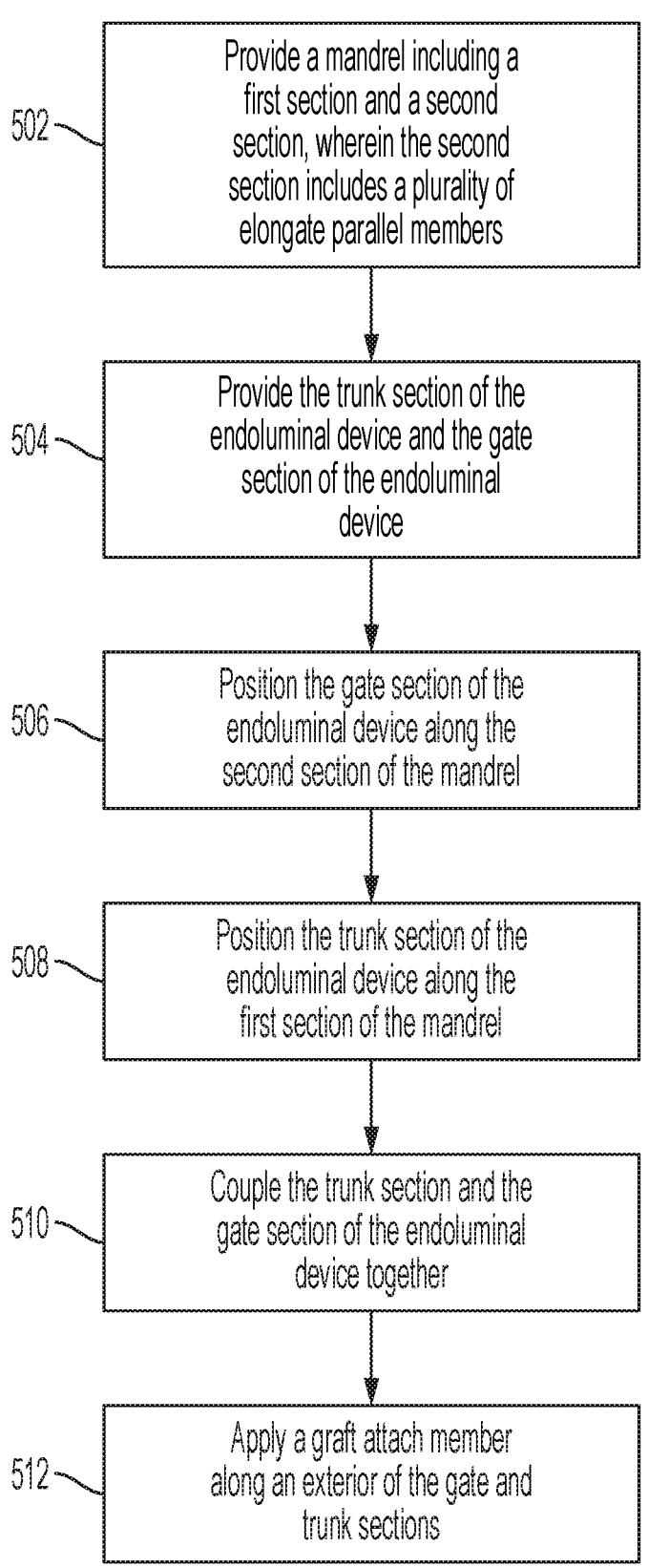

502 — Provide a mandrel including a first section and a second section, wherein the second section includes a plurality of elongate parallel members 504 — Provide the trunk section of the endoluminal device and the gate section of the endoluminal device 506 — Position the gate section of the endoluminal device along the second section of the mandrel 508 — Position the trunk section of the endoluminal device along the first section of the mandrel 510 — Couple the trunk section and the gate section of the endoluminal device together 512 — Apply a graft attach member along an exterior of the gate and trunk sections

FIG. 5

BRANCH ENDOPROSTHETIC SYSTEMS, DEVICES, AND METHOD

CROSS-REFERENCE TO RELATED APPLICATION

This application is a national phase application of PCT Application No. PCT/US2020/017219, internationally filed on Feb. 7, 2020, which is herein incorporated by reference in its entirety for all purposes.

FIELD

The present disclosure relates to systems and methods of manufacture for branched vascular endoprosthetic systems.

BACKGROUND

There is a need for advanced devices, tools, systems and methods used for the endoluminal treatment of vascular diseases in regions of branch vessels and main vessel junctions, including diseases affecting the aorta, including the descending aorta, the internal and external iliac arteries, and the femoral arteries.

SUMMARY

Various examples related to endoprosthesis and associated methods of manufacturing the endoprosthesis are disclosed. Various disclosed concepts relate to the endoprosthesis having a first leg, a second leg, and a bifurcation. According to one example ("Example 1"), the method of manufacturing includes providing a mandrel having a first section and a second section, the second section including a first elongate element and a second elongate element. The method also includes providing a first tubular graft element having a first end and a second end.

The method also includes folding the first tubular graft element to define a fold region. The first leg is defined between the first end of the first tubular graft and the fold region, and the second leg is defined between the second end of the first tubular graft element and the fold region. The method also includes applying the first tubular graft over the second section such that the second elongate element extends through the second leg of the first tubular graft and out of the second end of the first tubular graft, and such that the fold region is situated between the first and second legs to define the bifurcation.

The method also includes forming a trunk portion of the endoprosthesis along the mandrel such that the trunk portion extends along a portion of the first section of the mandrel. The trunk portion including a tab that extends across the bifurcation of the first tubular graft element. The method also includes securing together the trunk portion and the first tubular graft element to form the endoprosthesis.

According to another example further to Example 1 ("Example 2"), the trunk portion is formed as a second tubular graft element that is thereafter applied over the first section of the mandrel and secured to the first tubular graft element.

According to another example further to Example 1 or 2 ("Example 3"), the method also includes applying a graft material to an exterior of the endoprosthesis such that the graft material extends along at least a portion of the first and second legs to maintain an alignment of the first and second legs.

According to another example further to any preceding Example ("Example 4"), a longitudinal axis of the first leg is parallel with a longitudinal axis of the second leg.

According to another example further to any preceding Example ("Example 5"), a first cut line is defined about a circumference of the tubular graft in a first region between the first and second ends. The graft element is incised along the first cut line about a portion of less than an entirety of the first cut line define a first incised portion and a first unincised portion.

According to another example further to Example 5 ("Example 6"), the first tubular graft element is folded along the first unincised portion to define the fold region.

According to another example further to Example 5 or 6 ("Example 7"), a second cut line is defined about a circumference of the tubular graft in a second region between the first and second ends that is longitudinally offset from the first region. The graft element is incised along the second cut line about a portion of less than an entirety of the second cut line to define a second incised portion and a second unincised portion. A third cut line extends between the first and second cut lines, the graft element being incised along the third line.

According to another example further to Example 7 ("Example 8"), the method also includes folding the first tubular graft element along the second unincised portion, the fold region including the folded first unincised portion and the folded second unincised portion.

According to another example further to Example 7 or 8 ("Example 9"), the first tubular graft is applied over the second section such that the fold portion extends between the first and second legs to define the bifurcation.

According to another example further to any one of Examples 7 to 9 ("Example 10"), an excess section is defined in a region bound between the first and second cut lines. The third cut line bisects the excess section. The first tubular graft is applied over the second section such that at least a portion of the excess section extends along the first portion of the mandrel away from the bifurcation.

According to another example further to Example 10 ("Example 11"), the portion of the excess section that extends along the first portion of the mandrel includes a first flap and a second flap opposite the first flap. Free ends of each of the first and second flaps are defined by the third cut line.

According to another example further to any preceding Example ("Example 12"), the method also includes applying a support structure to the endoprosthesis along the trunk portion.

According to another example further to Example 12 ("Example 13"), the support structure is a stent.

According to another example further to Example 12 or 13 ("Example 14"), the support structure is situated between the trunk portion and a graft material surrounding the trunk portion.

According to another example further to any one of Examples 1 to 11 ("Example 15"), the method also includes applying a support structure to the endoprosthesis along one or more of the first and second legs.

According to another example further to Example 15 ("Example 16"), the support structure is a stent.

According to another example further to Example 15 or 16 ("Example 17"), the support structure is situated between the first tubular graft element and a graft material surrounding the first tubular graft element.

According to another example further to any preceding Example ("Example 18"), the first tubular graft is applied over the second section such that the first elongate element extends through the first leg of first tubular graft and out of the first end of the first tubular graft.

According to another example further to any preceding Example ("Example 19"), the tab extends between the first and second elongate elements.

Various examples related to multi-lumen graft devices and associated methods of constructing the same are also disclosed. Various disclosed concepts relate to the multi-lumen graft device having a main graft body and at least two graft legs. According to one example ("Example 20"), the method includes providing a mandrel with a main mandrel body and at least two mandrel legs, applying over the mandrel a single tubular structure that overlays each of the two mandrel legs and includes at least one tab that overlaps at least a portion of the main mandrel body, and forming the main graft body over the main mandrel body, the main graft body bonded to the at least one tab and positioned to overlap at least a portion of both of the two graft legs.

According to another example further to Example 20 ("Example 21"), at least one stent element is attached to the graft device.

According to another example further to Example 20 or 21 ("Example 22"), the single tubular structure includes at least two tabs, each tab being bonded to the main graft body.

According to another example further to any one of Examples 20 to 22 ("Example 23"), the main mandrel body includes at least one flat taper towards the two mandrel legs, and the flat taper defines a transition between the main mandrel body and the mandrel legs.

According to another example further to Example 23 ("Example 24"), at least one tab is aligned over the flat taper during construction.

While multiple embodiments are disclosed, still other embodiments will become apparent to those skilled in the art from the following detailed description, which shows and describes illustrative examples. Accordingly, the drawings and detailed description are to be regarded as illustrative in nature and not restrictive.

BRIEF DESCRIPTION OF THE DRAWINGS

The features and advantages of the present disclosure will become more apparent from the detailed description set forth below when taken in conjunction with the drawings.

FIG. 5 illustrates a method of manufacturing an endoluminal device, according to some embodiments.

4

Figure 9A:
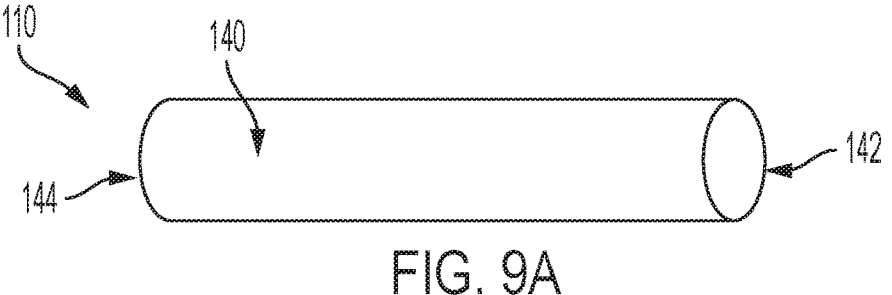
FIGS. 9A-9C illustrate various interim configurations of a trunk section of an endoluminal device during its manufacture, according to some embodiments.
Figure 9B:
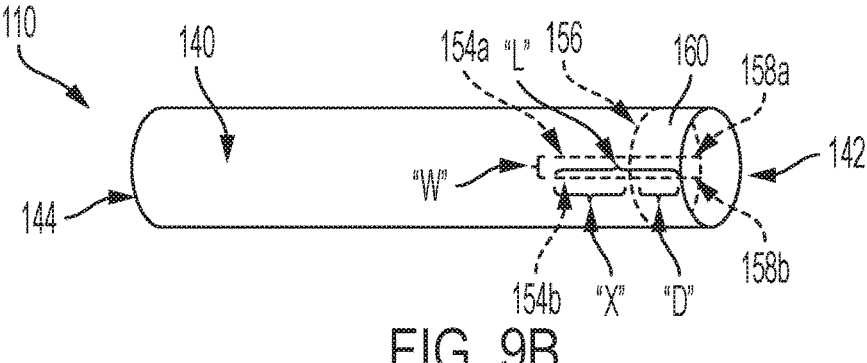
Figure 9C:
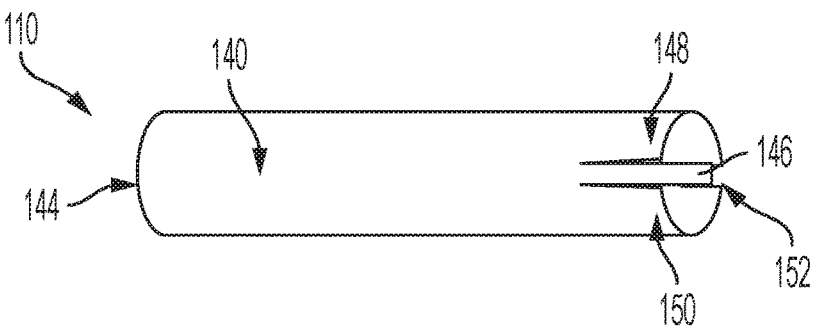
Figure 9D:
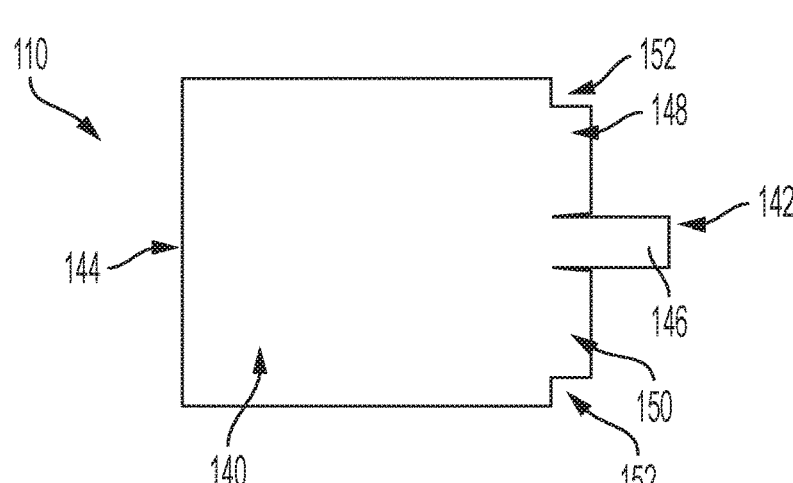

FIG. 9D is a representation of the trunk section of the endoluminal device shown in FIG. 9C that has been unrolled to a flat orientation, according to some embodiments.

Figure 10A:
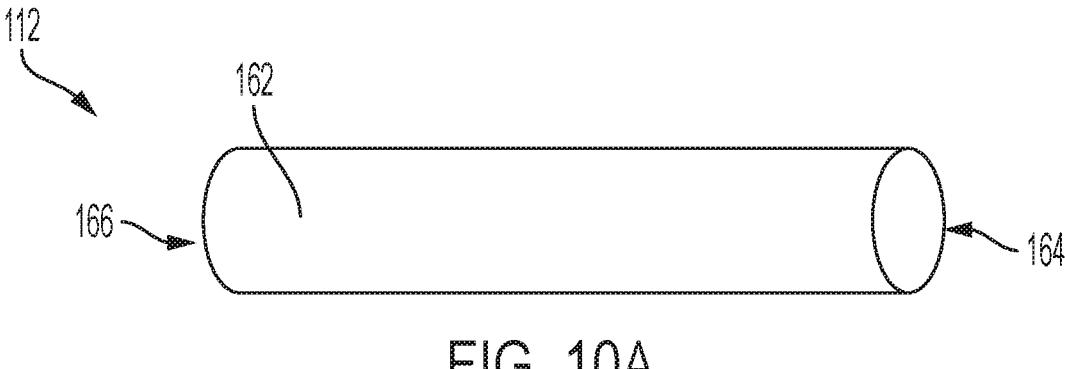
Figure 10B:
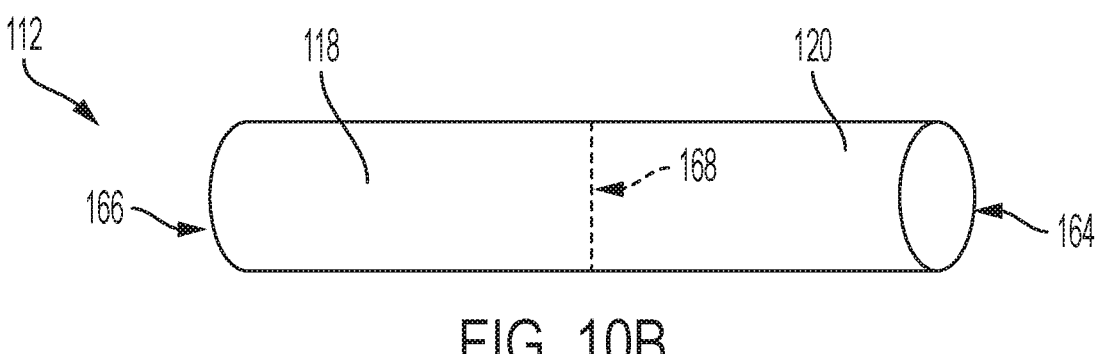
Figure 10C:
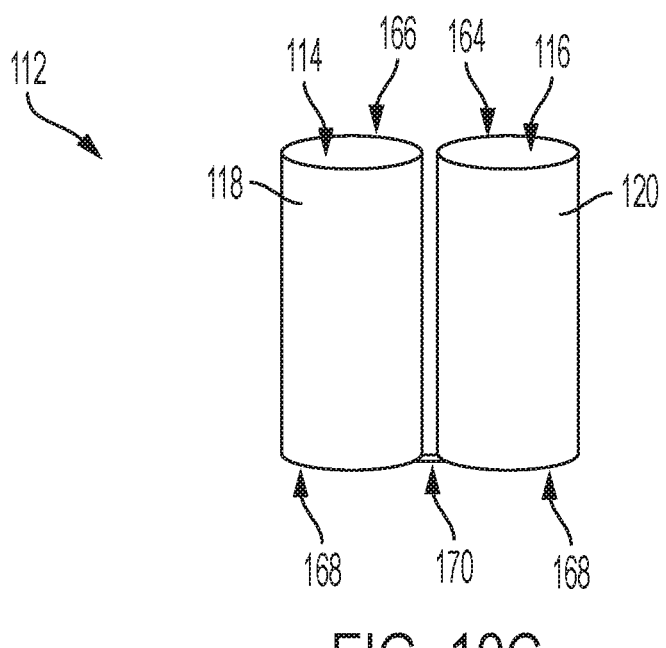

FIGS. 10A-10C illustrate various interim configurations of a gate section of an endoluminal device during its manufacture, according to some embodiments.

FIGS. 11A-11D illustrate various interim configurations of a gate section of an endoluminal device during its manufacture, according to some embodiments.

FIGS. 12A-12H illustrate various interim configurations of an endoluminal device during its manufacture, according to some embodiments.

DETAILED DESCRIPTION

Persons skilled in the art will readily appreciate that various aspects of the present disclosure can be realized by various methods and apparatuses configured to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms endoprosthetic device, endoprosthesis, vascular device, endoluminal device, and the like can refer, throughout the specification and in the claims, to any medical device capable of being implanted and/or deployed within a body lumen. In various embodiments, an endoprosthesis can comprise a stent, a stent-graft, a graft, and the like.

Throughout this specification and in the claims, the term "distal" refers to a location that is, or a portion of an endoluminal device (such as a stent-graft) that when implanted is, further downstream with respect to blood flow than another portion of the device. Similarly, the term "distally" refers to the direction of blood flow or further downstream in the direction of blood flow.

The term "proximal" refers to a location that is, or a portion of an endoluminal device that when implanted is, further upstream with respect to blood flow than another portion of the device. Similarly, the term "proximally" refers to the direction opposite to the direction of blood flow or upstream from the direction of blood flow.

With continuing regard to the terms proximal and distal, this disclosure should not be narrowly construed with respect to these terms. Rather, the devices and methods described herein may be altered and/or adjusted relative to the anatomy of a patient. Thus, it is to be appreciated that, where explicitly indicated, the terms "distal" and "distally" may refer to a relative location that is farther from a location in the body at which the medical device was introduced, or to a relative location that is farther from a physician operating the medical device. Similarly, where explicitly indicated, the terms "proximal" and "proximally" may refer to a relative location that is closer to the location in the body at which the medical device was introduced, or to a location that is closer to a physician operating the medical device.

As used herein, the term "vessel" refers to any luminal or tubular structure within the body to which these constructs can be utilized. This includes, but is not limited to, vascular blood vessels, vascular defects such as arteriovenous malformations, aneurysm, or others, vessels of the lymphatic system, esophagus, intestinal anatomy, sinuous cavity, urogenital system, or other such systems or anatomical features.

Endoluminal devices such as those discussed herein are used to treat the vasculature of mammalian patients. These treatments or procedures are commonly referred to as intraluminal or endovascular procedures. Such endoluminal devices, including stents and stent-grafts, can be generally tube-like structures that define one or more lumens and that can be inserted into the vasculature to open and/or maintain the vasculature in order to prevent or address localized flow constriction, weakening of the vasculature wall, aneurysms, etc. Thus, in various embodiments, the endoluminal device has dimensions appropriate for the desired vascular treatment and with sufficient strength to provide structural support for the flexible wall of the endoluminal device and/or the vasculature.

In some instances, endoluminal devices may include a proximal end and a distal end, with a single lumen extending from the proximal end to the distal end. In some other instances, an endoluminal device may include a proximal end and a distal end, where a plurality of lumens are defined at one or more of the proximal and distal ends. In some examples, an endoluminal device may include a bifurcation such that a lumen of the endoluminal device transitions to, or is otherwise divided into, a plurality of lumens. In some examples, the endoluminal device may include a plurality of lumens that each include such bifurcations.

FIGS. 1-4 illustrate an endoluminal device 100 in accordance with the present disclosure. The endoluminal device 100 can have various configurations, and generally includes, for example, a graft component 102 and a support component 104, where the support component 104 is configured to provide support to the graft component 102. The support and graft components 104 and 102 may be coupled together so that they are generally coaxial with one another. The endoluminal device 100 includes a proximal end 106 and a distal end 108, and generally includes a trunk section 110 and a gate section 112. Endoluminal device 100 may be a balloon expandable device, or may be of another configuration, including a self-expandable device, as those of skill in the art should appreciate.

Figure 2:
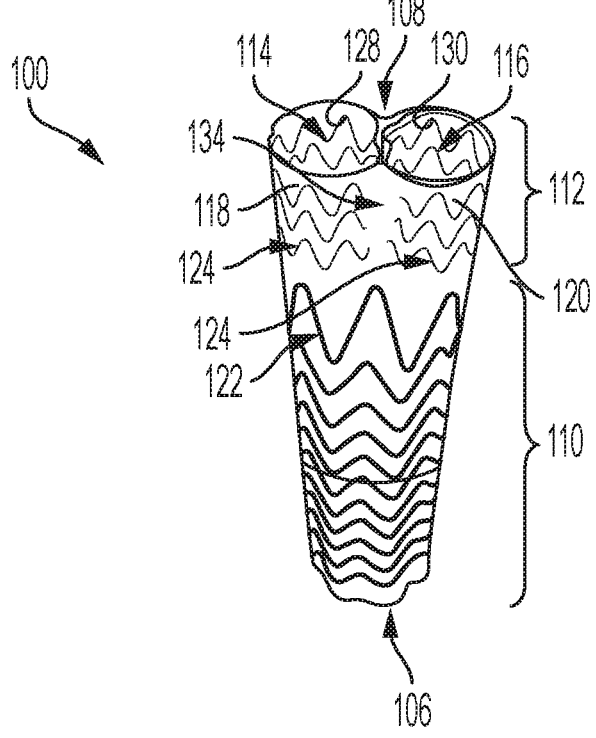
FIG. 2 is another perspective view of the endoluminal device of FIG. 1.

As discussed in greater detail below, in various examples, the trunk section 110 includes a single lumen, such as a trunk lumen, and the gate section 112 includes a bifurcation such that the gate section 112 includes a plurality of lumens, where the plurality of lumens of the gate section 112 are fluidly coupled with the lumen of the trunk section 110. FIG. 2 is a perspective view of the endoluminal device 100 showing the distal end 108 including the plurality of lumens, where the plurality of lumens includes a first gate lumen 114 and a second gate lumen 116. As shown, the first gate lumen 114 is defined, at least in part, by a first gate 118, while the second gate lumen 116 is defined, at least in part, by a second gate 120. Accordingly, it is to be appreciated that the gate section 112 includes the first gate 118 and the second gate 120.

The graft component 102 of the endoluminal device 100 may be made up of any material which is suitable for use as a graft in the chosen body lumen. Many graft materials are known, particularly known are those used as vascular graft materials. For instance, natural materials such as collagen may be introduced onto the inner surface of the stent and fastened into place. Synthetic polymers such as polyethylene, polypropylene, polyurethane, polyglycolic acid, polyesters, polyamides, their mixture, blends, copolymers, mixtures, blends and copolymers are also suitable. Included in this class are polyesters such as polyethylene terephthalate including DACRON and MYLAR and polyaramids such as KEVLAR, polyfluorocarbons, and porous or nonporous polyurethanes. Included in the class of fluoropolymers are polytetrafluoroethylene (PTFE), with and without copolymerized hexafluoropropylene, expanded or not-expanded PTFE, fluorinated ethylene propylene (FEP), copolymers of tetrafluoroethylene (TFE), and perfluoro (propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinylfluoride (PVF).

In addition, one or more radio-opaque metallic fibers, such as gold, platinum, platinum-tungsten, palladium, platinum-iridium, rhodium, tantalum, or alloys or composites of these metals may be incorporated into the device, particularly, into the graft, to allow fluoroscopic visualization of the device.

The graft materials may also be reinforced using a network of small diameter fibers. The fibers may be random, braided, knitted or woven.

FEP and other adhesive materials known in the art may be used as an adhesive for the graft materials. For instance, porous expanded polytetrafluoroethylene (ePTFE) graft component 102 may be formed by coupling together layers of ePTFE using an FEP adhesive. For instance, the ePTFE may be coated with FEP, or the FEP may be in the form of a coupling member (e.g., a flat ribbon) that is positioned between layers of the graft material. As discussed further below, FEP and other adhesive materials known in the art may additionally or alternatively be used to couple together the support component 104 and graft component 102.

In various examples, the support component 104 can include a steel, such as stainless steel or other alloy. In some examples, with support component 104 can include a shape memory alloy, such as, for example, Nitinol. In yet other examples, the support component can include a non-metallic material, such as a polymeric material. Accordingly, it is to be appreciated that the support component 104, including one or more discrete portions thereof, can be permanent (i.e., non-bioabsorbable) or bioabsorbable.

In some examples, the support component 104 is generally constructed of a reasonably high strength material, such as one which is resistant to plastic deformation when stressed, for example. The support component 104 may include a wire which is wound around a mandrel having pins arranged thereon so that the helical turns and undulations can be formed simultaneously. Other constructions also may be used. For example, an appropriate shape may be formed from a flat stock and wound into a cylinder or a length of tubing formed into an appropriate shape. Other suitable manufacturing methods include support components cut from a continuous tube (e.g., a laser cut nitinol tube).

In some examples, suitable materials include those that are suitably springy even when fashioned into very thin sheets or small diameter wires. For instance, consistent with the above, a variety of materials including metallic and superelastic alloys are suitable for use in the support component 104. Various stainless steels that have been physically, chemically, and otherwise treated to produce high springiness are also suitable, as are other metal alloys such as cobalt chrome alloys (e.g., ELGILOY), platinum/tungsten alloys, and the nickel-titanium alloys generically known as "nitinol". In some examples, other materials suitable as the support component include certain polymeric materials, particularly engineering plastics such as thermotropic liquid crystal polymers ("LCP's").

With continued reference to FIGS. 1-4, in various examples, the support component 104 includes one or more elements positioned along the trunk section 110, as well as one or more components positioned along the gate section 112.

For example, as shown, the support component 104 includes a plurality of ringed stent elements 122 positioned along the trunk section 110, as well as a plurality of ringed stent elements 124 positioned along the gate section 112. The ringed stent elements 122 and 124 may include a plurality of individual continuous cylindrically shaped components that are positioned adjacent to one another along a longitudinal axis of the endoluminal device or may include one or more helical windings, or a combination thereof.

In some examples, one or more of the adjacently situated ringed stent elements 122 and 124 can be interconnected with one another, such as, for example, via an interconnecting component (e.g., an interconnecting wire). In some such examples, the interconnecting wire may include a wire extending longitudinally between a first ringed stent element and a second adjacently situated ringed stent element. Any number of adjacently situated ringed stent elements may be coupled together via such interconnecting wires. In some other examples, in lieu of or in addition to such interconnecting wires, one or more apices 132 of a ringed stent element can be in contact with and connected to one or more of the apices 132 of an adjacently situated ringed stent element.

Figure 1:
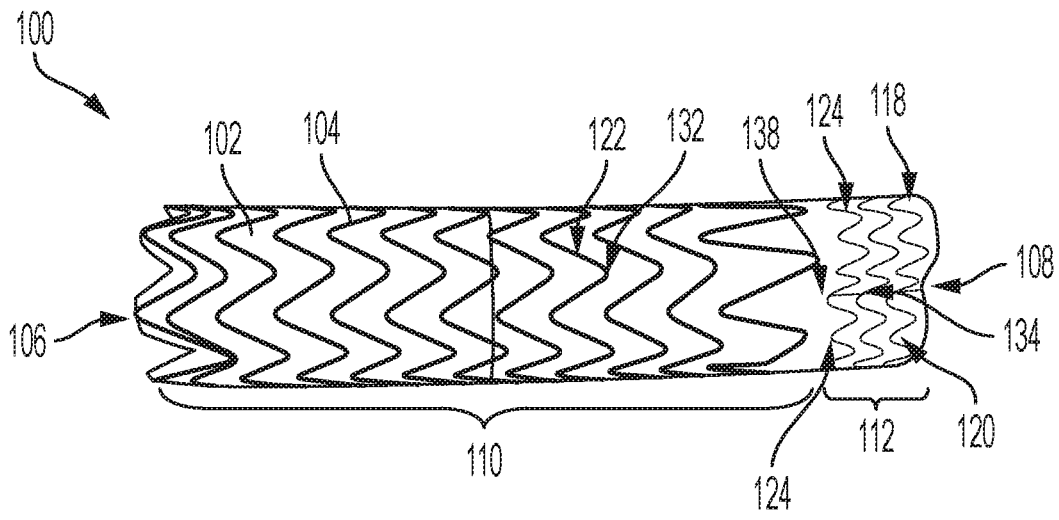
FIG. 1 is an illustration showing a perspective view of an endoluminal device, according to some embodiments.

The ringed stent elements 122 and 124 can be evenly spaced from each other along the longitudinal axis (i.e., uniformly distributed along the longitudinal axis), or may be spaced apart from one another at different spacing along the longitudinal axis (i.e., non-uniformly distributed along the longitudinal axis), or a combination thereof (e.g., as shown in FIG. 1). Accordingly, it is to be appreciated that any arrangement of the ringed stent elements 122 and 124 is within the scope of the present disclosure, provided that the ringed stent elements 122 and 124 are adapted to provide support to the trunk and gate sections 110 and 112.

In various embodiments, the various ringed stent elements 122 and 124 can vary from each other in stiffness. For example, one or more ringed stent elements 122 and 124 having an increased stiffness can be located at a distal and/or proximal end of the endoluminal device 100. Further, one or more ringed stent elements 122 and 124 having reduced stiffness can be located away from a distal and/or proximal end of the endoluminal device 100.

Moreover, while the ringed stent elements 122 and 124 of the endoluminal device 100 illustrated in FIGS. 1-4 comprises a generally sinusoidal configuration having a plurality of peaks and a plurality of valleys, it is to be appreciated that other configurations are contemplated, including ringed stent elements having any pattern that provides sufficient resilience and flexibility to endoluminal device 100. For instance, the ringed stent elements 122 and/or 124 may include a polygonal shape, such as, for example, a parallelogram. In various examples, the ringed stent elements 122 and/or 124 may be diamond shaped. In other embodiments, the ringed stent elements 122 and/or 124 may comprise a square or rectangular shape. Thus, it is to be appreciated that any shape of the ringed stent elements 122 and/or 124, including shapes that are not polygonal (such as ovoid or rounded shapes) or shapes that include undulations or bends, are within the scope of the present disclosure.

Consistent with the discussion above, in various examples, the ringed stent elements 122 and/or 124 may include a metal material, such as, steel, including stainless steel, or other alloy, including a shape memory alloy, such as, for example, Nitinol. In yet other embodiments, the ringed stent elements 122 and/or 124 may include a non-metallic material, such as a polymeric material. The ringed stent elements 122 and/or 124 may therefore be cut from a single metallic or polymeric tube according to known methods, if desired. Additionally or alternatively, the ringed stent elements 122 and/or 124 can be formed by using other known stent forming devices, such as a plurality of pins placed in an arrangement that corresponds with the desired pattern, where a wire is wound through the pins.

In some examples, the support component 104 is positioned concentrically around the graft component 102. In some other examples, the graft component 102 is positioned concentrically around the support component 104. In yet some other examples, the support component 104 may be positioned between layers of graft material of the graft component 102.

As such, in some examples, the graft material may define a luminal surface 126 of the trunk section 110, and/or a luminal surface 128 of the first gate 118, and/or a luminal surface 130 of the second gate 120, where such luminal surfaces are adapted to contact blood flow within a vessel when the endoluminal device 100 is implanted within the vasculature.

With continued reference to FIGS. 1-4, in various examples, the endoluminal device 100 is configured such that the first and second gates 118 and 120 are secured against substantial movement relative to one another. In some examples, such securement includes directly coupling together the first and second gates 118 and 120, such as, by way of stitching or adhesive such that the first and second gates 118 and 120 are affixed to one another. Alternatively, in some examples, the first and second gates 118 and 120 may be secured against movement relative to one another (and therefore effectively coupled together) without requiring a direct coupling between the first and second gates 118 and 120. That is, in some examples, the first and second gates 118 and 120 can be coupled together while maintaining a separation between the first and second gates 118 and 120 along their longitudinal lengths.

Figures 3, 4:
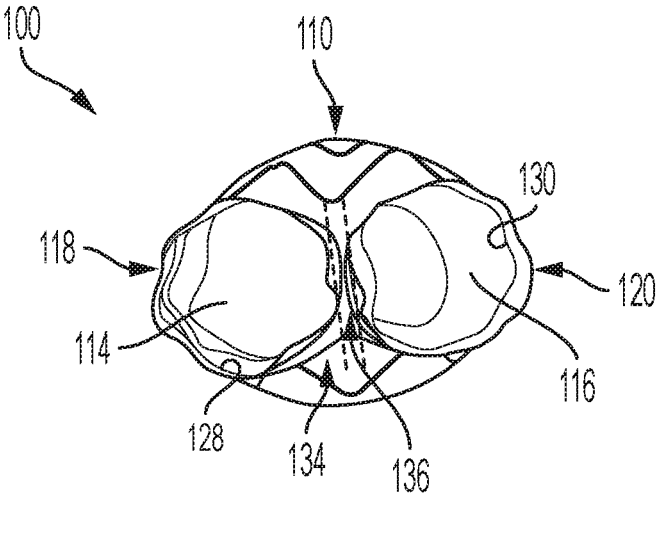
FIG. 3 is a first end view of the endoluminal device of FIG. 1, according to some embodiments.
FIG. 4 is a second end view of the endoluminal device of FIG. 1, according to some embodiments.

For example, as shown in FIGS. 1-4, the endoluminal device 100 includes a sleeve portion 134 that extends along an exterior of each of the first and second gates 118 and 120. In some examples, the sleeve portion 134 is integrated into the graft component 104 of the endoluminal device 100, as discussed in greater detail below. In various examples, the sleeve portion 134 includes graft material that has been wrapped about the first and second gates 118 and 120. As such, the wrapped graft material contacts a portion of less than all of the first and second gates 118 and 120 and forms a webbing that extends between and spans a gap 136 between the first and second gates 118 and 120, as shown in FIG. 3. In various examples, the gap 136 extends along the length of the first and second gates 118 and 120 from a bifurcation 138 to the distal end 108 of the endoluminal device 100. In various examples, the bifurcation 138 can be understood to be positioned at a distal end of the trunk component 110 and the proximal ends of each of the first and second gates 118 and 120 (the position of the bifurcation 138 along the endoluminal device 100 is shown in FIG. 1). In various examples, the bifurcation 138 can define one or more of the distal end of the trunk component 110 and the proximal ends of each of the first and second gates 118 and 120. Those of skill in the art should appreciate that the bifurcation 138 defines the division where the lumen of the trunk component 110 transitions into the respective first and second gate lumens 114 and 116.

It should be appreciated that the sleeve 134 is adapted to maintain alignment of the first and second gates 118 and 120, including the first and second gate lumens 114 and 116, which can help facilitate ease of cannulation of one or more of the first and second gate lumens 114 and 116. Furthermore, in some examples, the sleeve 134 can also increase the strength of the endoluminal device 100, such as the burst strength of the graft component 104 during deployment of its branches (e.g. the first gate 118 and the second gate 120) into the branch vessels. Also, in some examples, the sleeve 134 eases the process of deploying the endoluminal device 100 into a vessel because the plurality of ringed stent elements 124 are sandwiched between layers of the graft material, which in this case are the sleeve 134 on the outside and the graft component 102 on the inside, and thus reduces the friction which may result from the ringed stent elements 124 directly contacting the surrounding tissue walls.

Turning now to FIG. 5, an example method for manufacturing the endoluminal device 100 is illustrated. It is to be appreciated, however, that the illustrated method of manufacture of FIG. 5 is not intended to be limiting. As such, it is to be appreciated that the sequencing of steps, or the detailed steps discussed below, may be rearranged or completed in an alternative manner.

Figure 6A:
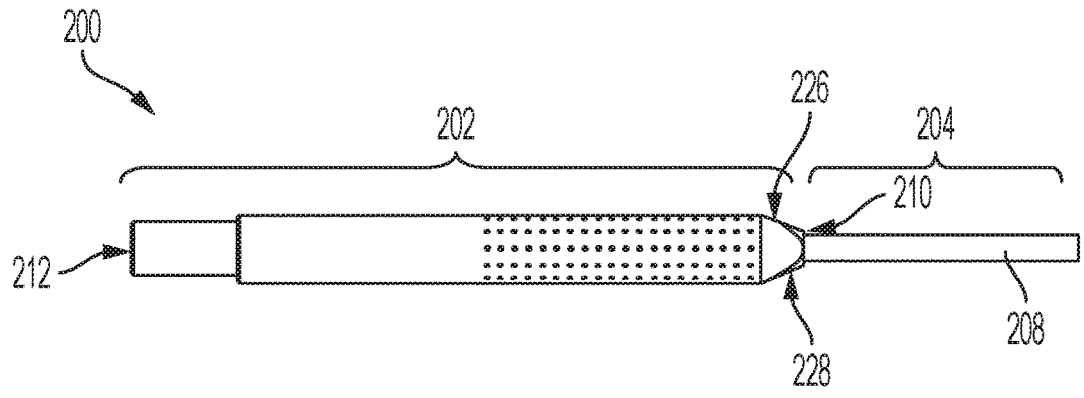
FIGS. 6A-6C illustrate a mandrel for use in the manufacture of an endoluminal device, according to some embodiments.
Figure 6B:
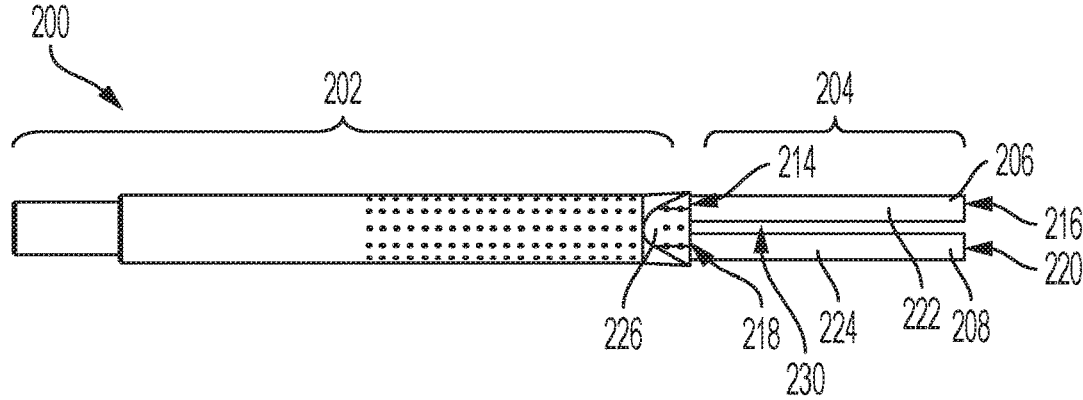
Figure 6C:
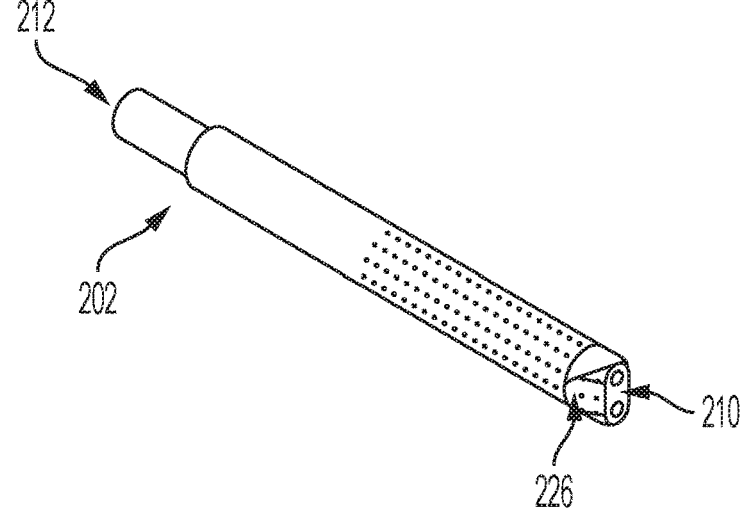

As shown, at step 502, a mandrel is provided that includes a first section and a second section, wherein the second section includes a plurality of elongate parallel members. An example mandrel 200 is shown in FIGS. 6A-6C. As shown, the mandrel 200 includes a first section 202 and a second section 204. The second section 204 includes a first elongate element 206 and a second elongate element 208, where the second elongate element 208 extends parallel to the first elongate element 206. The first and second elongate elements 206 and 208 extend from a distal end 210 of the first section 202, which is situated opposite a proximal end 212 of the first section 202. The first elongate element 206 includes a proximal end 214 and a distal end 216. Similarly, the second elongate element 208 includes a proximal end 218 and a distal end 220. The first and second elongate elements 206 and 208 include body portions 222 and 224, respectively, that are generally cylindrically shaped. Likewise, the first section 202 is cylindrically shaped, as shown.

As shown in FIG. 6B the proximal ends 214 and 218 of the first and second elongate elements 206 and 208 are coupled to the distal end 210 of the first section 202. In various examples, the first and second elongate elements 206 and 208 are coupled to the first section 202 such that they are laterally separated from one another. For example, as shown in FIG. 6B, the first and second elongate elements 206 and 208 are coupled to the first section 202 such that they are laterally separated from one another, as evidenced by a gap 230 between the first and second elongate elements 206 and 208 along their lengths. Put differently, the first and second elongate elements 206 and 208 are positioned such that a distance between the longitudinal axes of the first and second elongate elements 206 and 208 exceeds a sum of half the diameter of the first elongate element 206, half the diameter of the second elongate element 208, the thickness of the first gate 118, and the thickness of the second gate 120. In some examples, the first and second gates 118 and 120 have the same thickness. In some examples, the first and second elongate sections 206 and 208 have the same diameter. It will also be appreciated that the diameter of the first and second sections 206 and 208 corresponds to a luminal diameter of the first and second gates 118 and 120, respectively. In some examples, the first and second gates 118 and 120 are longitudinally offset from each other, e.g. by making the first elongate element 206 having a different length from the second elongate element 208 such that when viewed from the side, the first and second gates 118 and 120 do not align with each other.

The gap 230 coincides with the gap 136 formed between the first and second gates 118 and 120 discussed above. That is, the first and second elongate elements 206 and 208 are coupled to the first section 202 such that the gap 136 between the first and second gates 118 and 120 of the endoluminal device 100 can be formed during manufacture of the endoluminal device 100, as discussed further below.

In various examples, the first section 202 of the mandrel 200 is configured such that it includes a first tapered section 226 and a second tapered section 228, opposite the first tapered section 226, where the first and second tapered sections 226 and 228 are situated at the distal end 210 of the first section 202. In various examples, the first and second tapered sections 226 and 228 at the distal end 210 of the first section 202 provide for a transition of the trunk portion 110 of the endoluminal device 100 to the gate portion 112 of the endoluminal device 100. Such a transition provides for flow dynamics through the endoluminal device 100 that help minimize stasis regions that can lead to thrombus formation. As shown in FIGS. 6A-6C, the first and second tapered section 226 and 228 have an angle of approximately 21 degrees relative to the longitudinal axis of the mandrel 200, but it is to be appreciated that any suitable angle between 0 and 90 degrees may be implemented.

Figure 7:
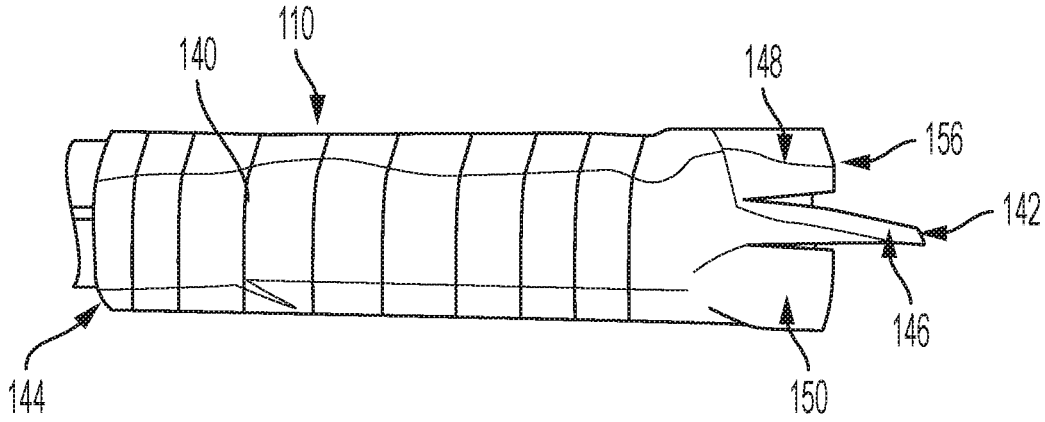
FIG. 7 illustrates a trunk section of an endoluminal device, according to some embodiments.
Figure 8:
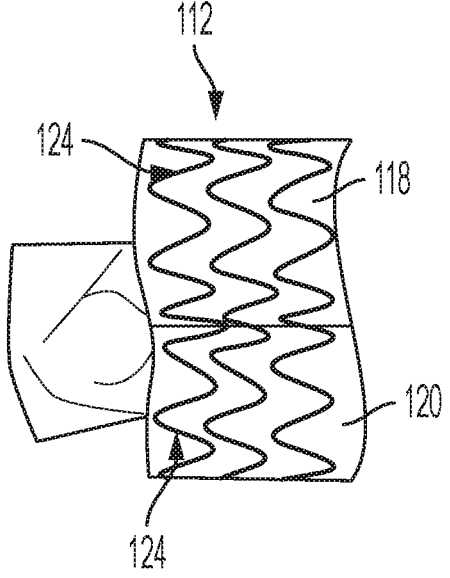
FIG. 8 illustrates a gate section of an endoluminal device, according to some embodiments.

As shown in FIG. 5, at step 504, the trunk and gate sections 110 and 112 of the endoluminal device 100 are provided. FIG. 7 provides an example illustration of the trunk section 110 in a pre-assembly configuration, and FIG. 8 provides an example illustration of the gate section 112 in a pre-assembly configuration. As shown in FIG. 7, the trunk portion 110 in the pre-assembly configuration includes a generally tubular body 140 having a distal end 142 and a proximal end 144. In various examples, the proximal end 144 of the tubular body 140 generally corresponds to the proximal end 106 of the endoluminal device 100. At its distal end 142, the trunk section 110 includes, in its pre-assembled configuration, a tail portion 146, a first overlap region 148, and a second overlap region 150. In some examples, the trunk section 110 includes a relief portion 152 that is situated opposite the tail portion 146 (see, e.g., FIG. 9C). As discussed in greater detail below, the relief portion 152 is configured such that tail portion 146 can be passed through it to form a saddle that extends across the distal end 142 of the trunk section 110 to help couple the gate section 112 with the trunk section 110.

As shown in FIG. 7, in various examples, the tubular body 140 of the trunk section 110 may be formed by disposing a graft material consistent with the graft materials discussed herein, along a mandrel. The graft material may be disposed about the mandrel by helically winding and/or longitudinally wrapping the graft material around a mandrel. Once the tubular body 140 is formed, it can be further processed to form the tail portion 146 and the first and second overlap regions 148 and 150.

Turning now to FIGS. 9A-9D, the trunk section 110 is shown in its pre-assembled configuration in various manufacturing steps. FIG. 9A shows the trunk section 110 after the tubular body 140 is formed and prior to formation of the tail portion 146 and the first and second overlap regions 148 and 150. FIG. 9B shows an example cut pattern on the trunk section 110 consistent with the formation of the tail portion 146 and the first and second overlap regions 148 and 150. FIG. 9C shows an example of the trunk section 110 after formation of the tail portion 146 and the first and second overlap regions 148 and 150, which is consistent with the illustration of the trunk section 110 shown in FIG. 7. FIG. 9D is a representation of the trunk section 110 shown in FIG. 9C that has been longitudinally cut, opened, and laid flat to better illustrate the features of the trunk section 110. It is to be appreciated that the longitudinal cut extends from the proximal end 144 to relief portion 152, wherein the longitudinal cut bisects the width of the relief portion 152.

As shown in FIGS. 9C and 9D, and as previously mentioned above, in its pre-assembled configuration, the trunk section includes the tail portion 146, the first overlap region 148, and the second overlap region 150. Optionally, in some examples, the trunk section 110 further includes the relief portion 152, which is situated opposite the tail portion 146. In some examples, the tail portion 146 and the first and second overlap regions 148 and 150 are formed by cutting the tubular body 140 of the trunk section 110 along the cut lines 154a, 154b, and 156, shown in FIG. 9B. As shown, cut lines 154a and 154b are longitudinal cut lines extending along the tubular body 140 at length "L," while cut line 156 is a circumferential cut line that is made in the tubular body 140 about less than an entirety of the circumference of the tubular body 140 of the trunk section 110. As shown, cut line 156 is made in the tubular body 140 about the circumference of the tubular body 140 less than the width "W" of the tail portion 146. That is, the cut line 156 does not traverse across the width "W" of the tail portion 146. Also shown in FIG. 9B are cut lines 158a and 158b, which may optionally be made in the tubular body 140 of the trunk section 110 to form the relief 152, as described further below.

In some examples, the tail portion 146 is formed by cutting the tubular body 140 along cut lines 154a and 154b, and also by cutting along cut line 156, and removing an excess section 160. As shown, excess section 160 is defined as the region bound between the distal end 142 and the cut line 156, and the cut lines 154a and 154b.

FIG. 9C shows the trunk section 110 in the pre-assembled configuration with the excess section 160 removed. As shown, the cut lines 154a and 154b extend proximally a distance "X," that is equivalent to the difference between "L" and "D." As such, it is to be appreciated that the cut lines 154a and 154b extend proximal to the first and second overlap regions 148 and 150 such that a base of the tail portion 146 (e.g., where the tail portion 146 terminates into the tubular body 140) is proximal to the first and second overlap regions. Such a configuration provides that the first and second overlap regions may be positioned distal to the tail portion 146 when the tail portion 146 is folded across the tubular body 140 and passed through the relief portion 152 to couple the trunk portion 110 to the gate section 112, as discussed further below. Additionally, as shown, with the excess section 160 removed, the tail portion 146 extends distal to the first and second overlap regions 148 and 150. In some examples, the distal end of the tail portion 146 defines the distal end 142 of the trunk section 110 in the pre-assembled configuration (see, e.g., FIG. 9D).

As mentioned above, in some examples, cut lines 158a and 158b may optionally be made in the tubular body 140 of the trunk section 110, opposite the cut lines 154a and 154b. For instance, cut line 158a may be made 180 degrees opposite cut line 154b, and cut line 158b may be made 180 degrees opposite cut line 154a, as shown in FIG. 9B. In some examples, cut lines 158a and 158b may have a length equal to the difference between the length "L" of the tail portion 146 and the depth "D" of the excess portion 160. As such, it is to be appreciated that the cut lines 158a and 158b extend substantially the same amount proximally along the tubular body 140 of the trunk section 110 from the cut line 156 as do the cut lines 154a and 154b.

In various examples, a cut line (not shown) is made between the cut lines 158a and 158b at their proximal ends. Thus, the relief portion 152 is formed by removing the excess material defined between the cut line 156 and proximal end of the cut lines 158a and 158b, and between the cut lines 158a and 158b. In various examples, the cut lines 158a and 158b are separated by substantially the same width "W" as the cut lines 154a and 154b such that the relief portion 152 has substantially the same width "W" as does the tail portion 146.

It is to be appreciated that the tubular body 140 may be cut along the cut lines discussed above, including cut lines 154a, 154b, 156, 158a, and 158b, according to known methods, such as laser cutting.

It is to be appreciated that the width "W" can be any desired width less than the circumference of the tubular body 140 of the trunk section 110. It is also to be appreciated that the length "L" can be any desired length less than the longitudinal length of the trunk section 110 measured from the proximal end 144 to the distal end 142. It is also to be appreciated that the depth "D" can be any desired depth less than or equal to the difference between the diameter and the length "L" of the cut lines 154a and 154b.

Turning now to FIGS. 10A-10C, an example gate section 112 is shown in its pre-assembled configuration in various manufacturing steps. FIG. 10A shows the gate section 112 after the tubular body 162 is formed and prior to partially splitting the tubular body 162 to form the first and second gates 118 and 120. FIG. 10B shows an example cut pattern on the gate section 112 consistent with the formation of the first and second gate portions 118 and 120. FIG. 10C shows an example of the gate section 112 after partially splitting the tubular body 162 and folding the same to form the first and second gates 118 and 120.

In various examples, the tubular body 162 of the gate section 112 may be formed from disposing a graft material consistent with the graft materials discussed herein, along a mandrel. The graft material may be disposed about the mandrel according to known methods, such as by helically winding and/or longitudinally wrapping the graft material around a mandrel. Once the tubular body 162 is formed, it can be further processed to form the gate section 112.

As shown in FIG. 10C, in its pre-assembled configuration, the gate section 112 includes the first and second gates 118 and 120. In some examples, the first and second gates 118 and 120 are formed by cutting the tubular body 162 of the gate section 112 along the cut line 168, shown in FIG. 10B. As shown, cut line 168 is a cut made transverse to the longitudinal axis of the tubular body 162. The cut line 168 is made as a circumferential cut in the tubular body 162 about less than an entirety of the circumference of the tubular body 162 of the gate section 112. It is to be appreciated that any suitable length of cut may be used provided that the tubular body 162 can be folded so as to define the first and second gates 118 and 120 consistent with the discussion below. In some examples, the circumferential cut corresponds with a cut length corresponding to at least half of the circumference of the tubular body 162 in the region of the cut line 168. As shown, the first gate 118 is defined as the region bound between the proximal end 166 and the cut line 168, while the second gate 120 is defined as the region bound between the distal end 164 and the cut line 168.

FIG. 10C shows the gate section 112 in the pre-assembled configuration after the tubular body 162 has been cut to define the first and second gates 118 and 120. As shown, after cutting the tubular body 162 along the cut line 168 to define the first and second gates 118 and 120, the tubular body 162 is folded at the cut line 168 to draw the distal and proximal ends 164 and 166 toward one another until the first and second gates 118 and 120 extend substantially parallel with one another while being laterally offset with one another. That is, after folding the tubular body 162 along the cut line 168, the first and second gates 118 and 120 do not share a common axis or are otherwise not coaxial with one another. In various examples, despite not being coaxial with one another, the axes of the first and second gates 118 and 120 may nevertheless extend substantially parallel with one another, as shown in FIG. 10C.

Additionally, as mentioned above, the cut line 168 is a circumferential cut in the tubular body 162 about less than an entirety of the circumference of the tubular body 162 of the gate section 112. Accordingly, when folded to the pre-assembled configuration shown in FIG. 10C, the first and second gates 118 and 120 remain coupled together via the uncut portion 170 of the graft material of the tubular body 162. In various examples, the uncut portion 170 defines a saddle or otherwise supporting structure extending between the first and second gate 118 and 120 opposite the proximal and distal end 166 and 164 in the folded configuration shown in FIG. 10C. As discussed in greater detail below, this saddle or uncut portion 170 provides a support structure that helps couple the gate section 112 to the trunk section 110.

It is to be appreciated that the tubular body 162 may be cut along the cut lines discussed above, including cut line 168, according to known methods, such as laser cutting.

Figure 11A:
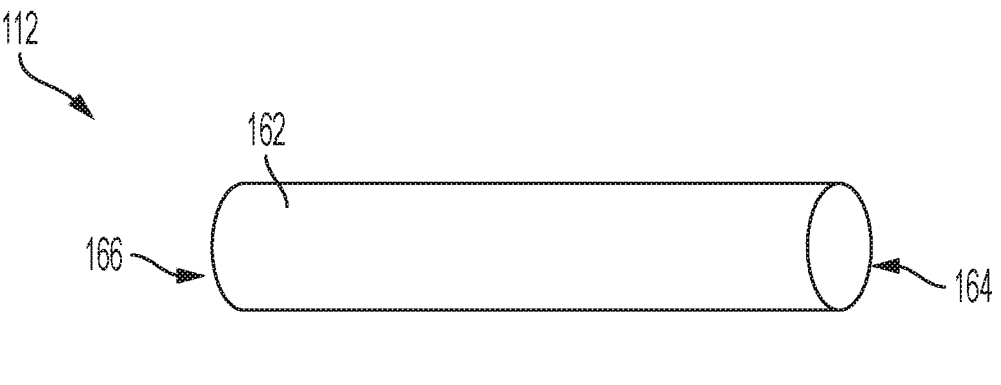
Figure 11B:
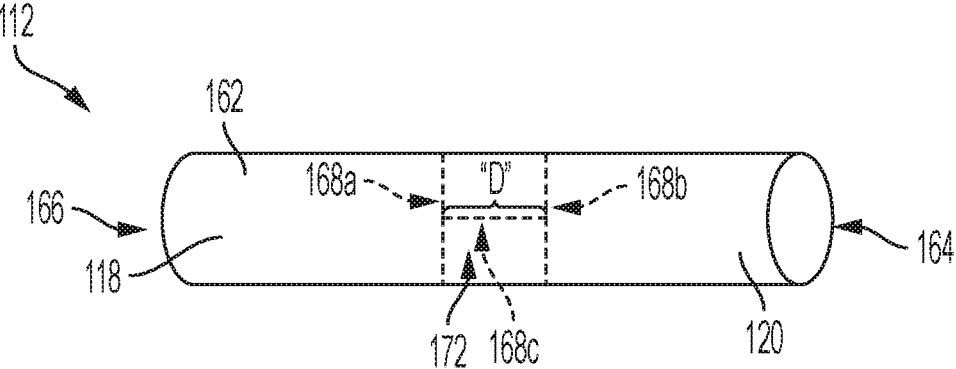
Figure 11C:
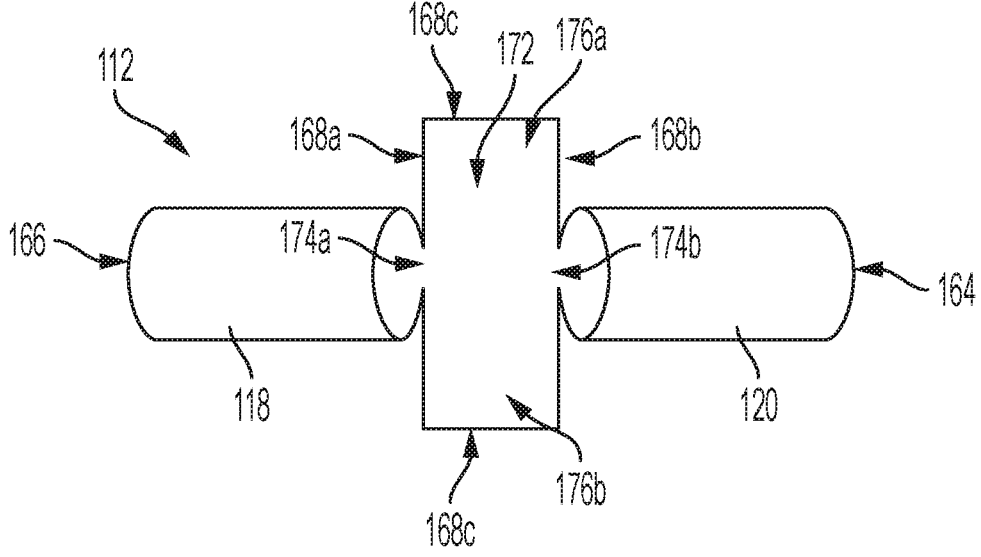
Figure 11D:
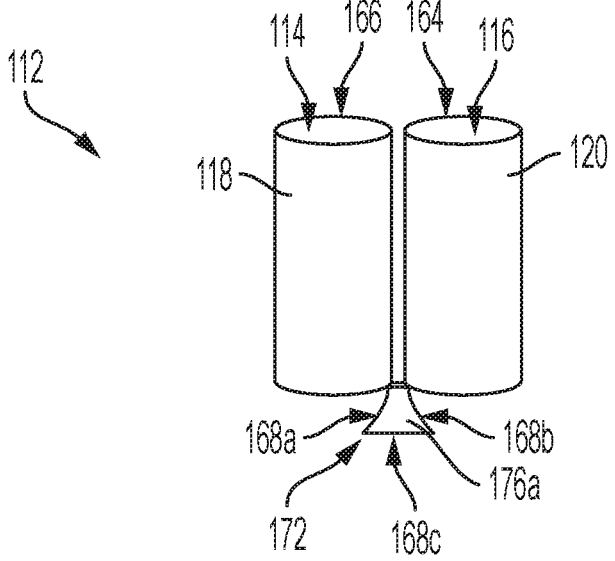

Turning now to FIGS. 11A to 11D, another example gate section 112 is shown in its pre-assembled configuration in various manufacturing steps. FIG. 11A shows the gate section 112 after the tubular body 162 is formed and prior to partially splitting the tubular body 162 to form the first and second gates 118 and 120. FIG. 11B shows an example cut pattern on the gate section 112 consistent with the formation of the first and second gate portions 118 and 120. FIG. 11C shows the tubular body 162 with portions of the cut graft material laid open prior to folding the tubular body 162 to the configuration shown in FIG. 11D. FIG. 11D shows an example of the gate section 112 after folding the tubular body 162 to form the first and second gates 118 and 120, which is consistent with the illustration of the gate section 112 shown in FIG. 8.

As discussed above, the tubular body 162 of the gate section 112 may be formed from disposing a graft material consistent with the graft materials discussed herein, along a mandrel. The graft material may be disposed about the mandrel according to known methods, such as by helically winding and/or longitudinally wrapping the graft material around a mandrel. Once the tubular body 162 is formed, it can be further processed to form the gate section 112 shown in FIGS. 11B-11D.

As shown in FIG. 11C, in its pre-assembled configuration, the gate section 112 includes the first and second gates 118 and 120. In some examples, the first and second gates 118 and 120 are formed by cutting the tubular body 162 of the gate section 112 along the various cut lines 168a to 168c, shown in FIG. 11B. As shown, cut lines 168a and 168b each correspond to cuts to be made transverse to the longitudinal axis of the tubular body 162. In the illustration shown in FIG. 11B, the cut lines 168a and 168b are each substantially perpendicular to the longitudinal axis of the tubular body 162. However, in some examples, the cut lines 168a and 168b may be angled relative to the longitudinal axis as desired, which will have the effect of producing an excess section (e.g., excess section 172) that tapers from its free ends. The cut lines 168a and 168b are longitudinally offset from one another a distance "D" as shown in FIG. 11B. The distance "D" may be any desired distance. These cut lines 168a and 168b are made as circumferential cuts in the tubular body 162 about less than an entirety of the circumference of the tubular body 162 of the gate section 112. It is to be appreciated that any suitable length of cut may be used provided that the tubular body 162 can be folded so as to define the first and second gates 118 and 120, as discussed further below. In some examples, the circumferential cut corresponds with a cut length corresponding to at least half of the circumference of the tubular body 162 in the region of the cut line 168. As shown, the first gate 118 is defined as the region bound between the proximal end 166 and the cut line 168a, while the second gate 120 is defined as the region bound between the distal end 164 and the cut line 168b.

An excess section 172 is defined in the region bound between the cut lines 168a and 168b, where cut line 168c bisects the excess section 172. In some examples, as discussed further below, the excess section 172 may define a saddle region of the gate section 112 that provides a support structure that helps couple the gate section 112 to the trunk section 110. In such examples, the saddle region is formed by cutting the tubular body 162 along cut lines 168a, 168b, and 168c, and folding open the excess section 172 as shown in FIG. 11C. Notably, as mentioned above, cut lines 168a and 168b are not full circumferential cuts, but are instead partial circumferential cuts. As such, the first and second gates 118 and 120 remain coupled together via the uncut portions 174a and 174b of the tubular graft, which are defined as the uncut regions between the excess portion 172 and each of the first and second gates 118 and 120, as shown in FIG. 11C.

FIG. 11D shows the gate section 112 in the pre-assembled configuration after the tubular body 162 has been cut to define the first and second gates 118 and 120. As shown, after cutting the tubular body 162 along the cut lines 168a, 168b, and 168c to define the first and second gates 118 and 120, the tubular body 162 is folded to draw the distal and proximal ends 164 and 166 toward one another until the first and second gates 118 and 120 extend substantially parallel with one another while being laterally offset with one another. That is, after folding the tubular body 162 in the manner shown in FIG. 11D, the first and second gates 118 and 120 do not share a common axis or are otherwise not coaxial with one another. In various examples, despite not being coaxial with one another, the axes of the first and second gates 118 and 120 may nevertheless extend substantially parallel with one another, as shown in FIG. 11D. In some examples, the first and second gates 118 and 120 have different lengths from each other. For example, when the cut line 168 in FIG. 10B or cut lines 168a to 168c in FIG. 11B are shifted toward the proximal end 166, the first gate 118 will be longitudinally shorter than the second gate 120, whereas when the cut line 168 or cut lines 168a to 168c are shifted closer to the distal end 164, the second gate 120 will be longitudinally shorter than the first gate 118.

Additionally, as mentioned above, the cut lines 168a and 168b are each partial circumferential cuts in the tubular body 162 about less than an entirety of the circumference of the tubular body 162 of the gate section 112. Accordingly, when folded to the pre-assembled configuration shown in FIG.

11D, the first and second gates 118 and 120 remain coupled together via the excess portion 172. In various examples, the excess portion 172 defines a saddle or otherwise supporting structure extending between the first and second gate 118 and 120 opposite the proximal and distal end 166 and 164 in the folded configuration shown in FIG. 11D. In various examples, the excess portion defines tabs 176a and 176b (see, e.g., FIGS. 11C and 11D). The tabs 176a and 176b correspond to those regions of the excess portion 172 that extend away from the uncut region of the excess portion 172 (e.g., the region where the excess portion 172 remains coupled with the first and second gates 118 and 120).

It is to be appreciated that the tubular body 162 may be cut along the cut lines discussed above, including cut lines 168a, 168b, and 168c, according to known methods, such as laser cutting.

Figure 12A:
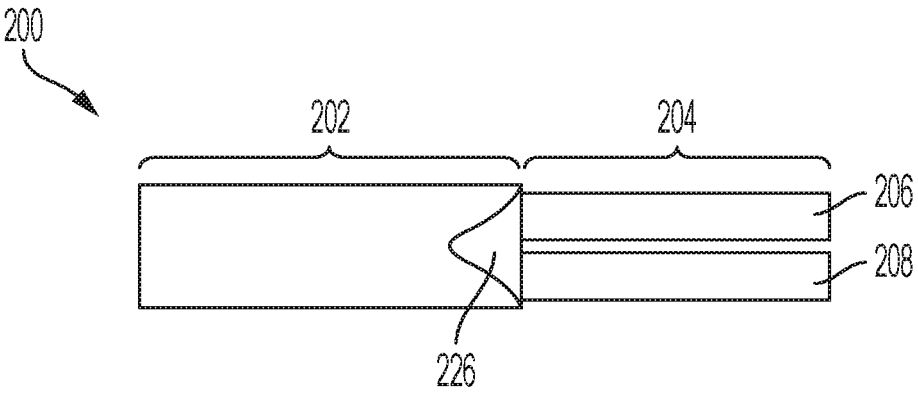
Figure 12B:
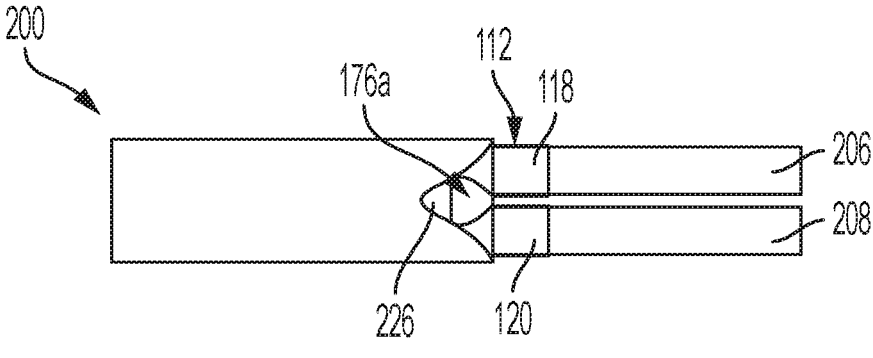

Referring back now to FIG. 5, at step 506, the gate section 112, in its pre-assembled configuration, is positioned along the second section 204 of the mandrel 200. Turning now to FIGS. 12A and 12B, the gate section 112 is shown being positioned along the second section 204 of the mandrel 200. FIG. 12A shows the mandrel 200 without the gate section 112 positioned thereon, and FIG. 12B shows the mandrel 200 with the gate section 112 positioned on the second section 204, adjacent the first section 202. In some examples, the gate section 112 may be positioned on the second section 204 in abutting contact with the distal end 210 of the first section 202 of the mandrel 200 (shown, for example, in FIGS. 6A and 6C). As shown in FIG. 12B, the gate section 112 is positioned along the second section 204 of the mandrel 200 such that the first elongate element 206 extends through the lumen 114 of the first gate 118 and such that the second elongate element 208 extends through the lumen 116 of the second gate 120. Additionally, as shown, the tab 176a is positioned along the first tapered section 226 of the first section 202 of the mandrel 200. Although not shown in the figures, it is to be appreciated that tab 176b is similarly situated along the second tapered section 228.

Additionally or alternatively, in some examples, prior to positioning the tabs 176a and 176b along the first and second tapered sections 226 and 228 (see, e.g., FIG. 12B), a separate length of graft material may optionally be applied to the mandrel such that it extends from the first tapered section 226 to the second tapered section 228, and across the portion of the distal end 210 between the first and second tapered sections 226 and 228 and between the first and second elongate elements 206 and 208 (e.g., within the gap 230) such that the tabs 176a and 176b are positioned at least partially on top of the separate length of graft material that is already applied to extend across the distal end 210. In some examples, the excess piece of graft material may be configured such that its width in the region of the gap 230 is consistent with the width between the first and second elongate elements 206 and 208 such that the excess piece of graft material lays substantially flat (e.g., essentially wrinkle free) against the distal end 210 of the first section 202 of the mandrel 200 in the region of the gap 230. Such a configuration helps minimize the potential for wrinkles or uneven surface structures along the interior region of the endoluminal device in the region of the bifurcation 138 of the endoluminal device 100. For instance, in configurations where the distance "D" of the cut line 168c (see, e.g., FIG. 11B) exceeds the width of the gap 230 (see, e.g., FIG. 6B) between the first and second elongate elements 206 and 208, the excess section 172 may be compressed longitudinally (e.g., cut lines 168a and 168b compressed toward one another) when the gate section 112 is loaded onto the second section 204 of the mandrel 200. This compression of the excess section 172 may result in the wrinkling of the excess section 172.

Figure 12C:
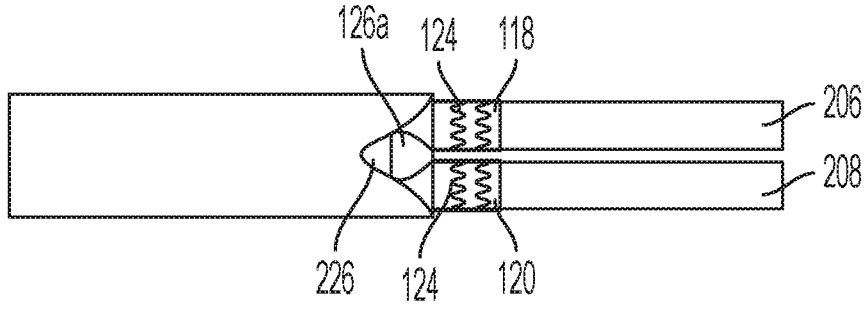

FIG. 12C shows a similar configuration to that shown in FIG. 12B, but for the addition of the ringed stent elements 124 applied to the first and second gates 118 and 120 of the gate section 112. In various examples, the ringed stent elements 124 are applied to the gate section 112 prior to loading the gate section 112 on the mandrel 200. In some other examples, the ringed stent elements 124 are applied to the gate section 112 after loading the gate section 112 on the mandrel 200. As mentioned above, the ringed stent elements 124 may be coupled with the gate section 112 according to known methods.

Figure 12D:
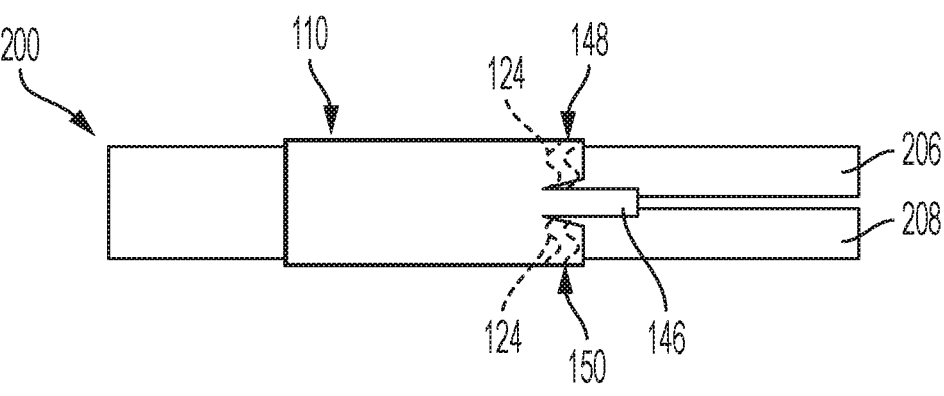

Referring back again to FIG. 5, at step 508, the trunk section 110, in its pre-assembled configuration, is positioned along the first section 202 of the mandrel 200. Turning now to FIG. 12D, the trunk section 110 is shown being positioned along the first section 202 of the mandrel 200. FIG. 12D shows the trunk section 110 positioned with the tail portion 146 extending distally. Additionally, as shown, the trunk section 110 is positioned along the mandrel 200 such that the trunk section 110 overlaps, at least in part, the gate section 112. For example, as shown in FIG. 12D, the trunk section 110 overlaps the gate section 112 such that the first and second overlap regions 148 and 150 overlap, at least in part, the first and second gates 118 and 120 (which are concealed from view by the first and second overlap regions 148 and 150 in FIG. 12D).

Figure 12E:
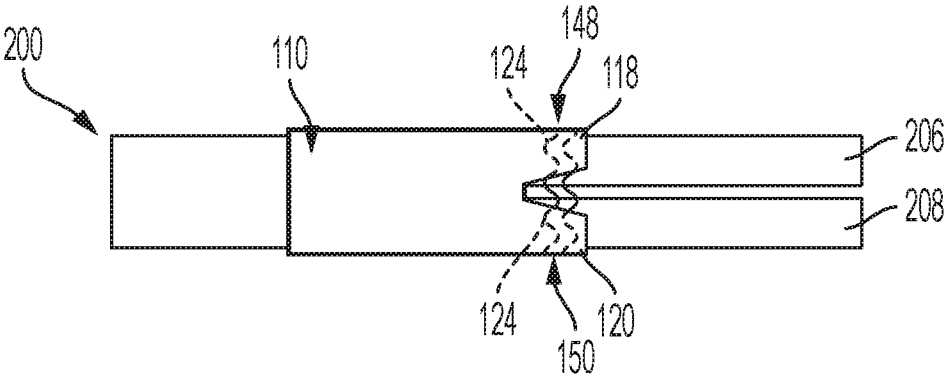

Referring back again to FIG. 5, at step 510, the trunk section 110 and the gate section 112 are coupled together. Turning now to FIG. 12E, the trunk section 110 is shown positioned with the tail portion 146 wrapped through the gap 230. Although not shown in the figures, it will be appreciated that the tail portion 146 is wrapped through the gap 230 and positioned along one or the other of the interior or exterior of the trunk section 110 along the second tapered section 228 of the mandrel 200. Such a configuration provides that the uncut portion (e.g., 170 or 172) of the tubular body 162 extending between the first and second gates 118 and 120 is positioned between the distal end 210 of the first section 202 of the mandrel 200 and the tail portion 146. The wrapped portion of the tail portion 146 may be secured or coupled with one or more of the trunk section 110, the gate section 112, and/or an optional piece of graft material, in the region of the second tapered section 228 of the mandrel 200. Securement or coupling of the tail portion 146 may be by way of one or more adhesives, or according to other known methods. By wrapping the tail portion 146 in such a manner, the trunk and gate sections 110 and 112 can be coupled together in at least the region of the bifurcation 138. In various examples, the first and second overlap regions 148 and 150 can be secured to the first and second gates 118 and 120 to further couple together the trunk and gate sections 110 and 112 to form the endoluminal device 100. It is to be appreciated that the first and second overlap regions 148 and 150 can be secured to the first and second gates 118 and 120 at this stage using one or more adhesives, or according to other known methods.

Figure 12F:
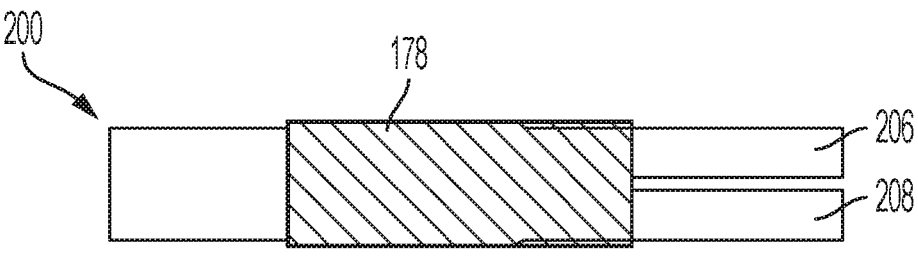
Figure 12G:
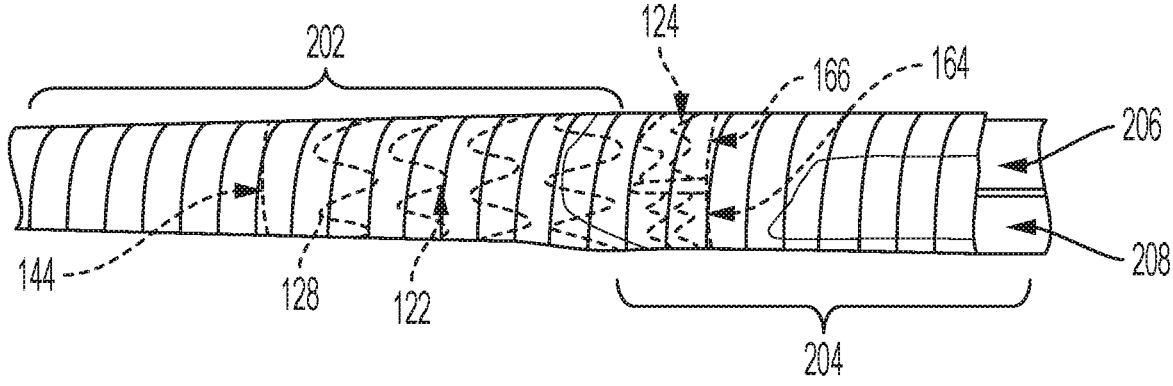

Referring back again to FIG. 5, at step 512, a graft attach member is applied along the trunk and gate sections 110 and 112. FIG. 12F provides an example illustration showing a graft attach member 178 wound around the trunk and gate sections 110 and 112. The graft attach member 178 may be any suitable graft material discussed above. It is to be appreciated that other suitable methods of disposing a graft attach member about the trunk and gate sections 110 and 112 may be used. For instance, a pre-made tubular graft attach member may be advanced over and positioned along the trunk and gate sections 110 and 112. In some examples, the graft attach member 178 may have a longitudinal length that exceeds a longitudinal length of the trunk and gate sections 110 and 112, as measured from the proximal end 144 of the trunk section 110 to the ends 164 and 166 of the first and second gates 118 and 120 when assembled on the mandrel 200. A representation of such a configuration is shown in FIG. 12G, where the graft attach member 178 is applied such that it extends proximal to the proximal end 144 of the trunk section 110 and distal to the ends 164 and 166 of the first and second gates 118 and 120.

In various examples, after applying the graft attach member 178 the assembly including at least the graft attach member 178 and the trunk and gate sections 110 and 112 are coupled together, which may be accomplished according to known methods, such as heating, applying pressure, compression, or a combination thereof.

In various examples, after bonding together one or more of the graft attach member 178 and the trunk and gate sections 110 and 112, the resulting assembly can be trimmed to a desired length to define the proximal and distal ends 106 and 108 of the endoluminal device 100. Trimming may occur before or after removing the assembly from the mandrel 200.

Figure 12H:
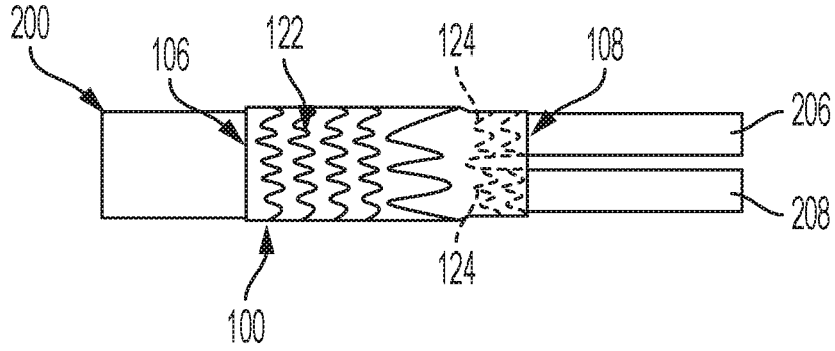

FIG. 12H shows the endoluminal device 100 loaded on the mandrel 200. The endoluminal device 100 is shown with ringed stent elements 122. The ringed stent elements 122 may be applied to the trunk section 110 prior to loading the trunk section 110 on the mandrel 200, or may be applied to the trunk section 110 after loading the trunk section 110 on the mandrel 200. For instance, the ringed stent elements 122 may be applied to the trunk section 110 after bonding the graft attach member 178 to the trunk and gate sections 110 and 112. In such a configuration, it will be appreciated that the ringed stent elements 122 are situated about an exterior of the graft attach member 178 while the graft attach member 178 is disposed about and exterior of the ringed stent elements 124, as shown in FIG. 12H. In some examples, one or more additional coatings of graft material may be applied about and exterior of the endoluminal device 100 such that the ringed stent elements 124 are situated between the graft attach member 178 and the additional coatings of graft material.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of manufacturing an endoprosthesis that includes a first leg, a second leg, and a bifurcation, the method comprising:

providing a mandrel having a first section and a second section, the second section including a first elongate element and a second elongate element;

providing a first tubular graft element having a first end and a second end;

cutting the first tubular graft element and folding the first tubular graft element to define a fold region, wherein the first leg is defined between the first end of the first tubular graft element and the fold region and wherein the second leg is defined between the second end of the first tubular graft element and the fold region, wherein an excess portion of the fold region between the first and second legs defines a tab extending away from an uncut region of the excess portion;

applying the first tubular graft element over the second section such that the second elongate element extends through the second leg of the first tubular graft element and out of the second end of the first tubular graft element, and such that the fold region is situated between the first and second legs to define the bifurcation;

forming a trunk portion of the endoprosthesis along the mandrel such that the trunk portion extends along a portion of the first section of the mandrel and the tab lays against a section of the trunk portion; and securing together the trunk portion and the first tubular graft element to form the endoprosthesis.

2. The method of claim 1, wherein the trunk portion is formed as a second tubular graft element that is thereafter applied over the first section of the mandrel and secured to the first tubular graft element.

3. The method of claim 1, further comprising applying a graft material to an exterior of the endoprosthesis such that the graft material extends along at least a portion of the first and second legs to maintain an alignment of the first and second legs.

4. The method of claim 1, wherein a longitudinal axis of the first leg is parallel with a longitudinal axis of the second leg.

5. The method of claim 1, further comprising applying a support structure to the endoprosthesis along the trunk portion.

6. The method of claim 5, wherein the support structure is a stent.

7. The method of claim 5, wherein the support structure is situated between the trunk portion and a graft material surrounding the trunk portion.

8. The method of claim 1, further comprising applying a support structure to the endoprosthesis along one or more of the first and second legs.

9. The method of claim 8, wherein the support structure is a stent.

10. The method of claim 8, wherein the support structure is situated between the first tubular graft element and a graft material surrounding the first tubular graft element.

11. The method of claim 1, wherein the first tubular graft element is applied over the second section such that the first elongate element extends through the first leg of the first tubular graft element and out of the first end of the first tubular graft element.

12. The method of claim 1, wherein the tab extends between the first and second elongate elements.

13. A method of manufacturing an endoprosthesis that includes a first leg, a second leg, and a bifurcation, the method comprising:

providing a mandrel having a first section and a second section, the second section including a first elongate element and a second elongate element;

providing a first tubular graft element having a first end and a second end;

folding the first tubular graft element to define a fold region, wherein the first leg is defined between the first end of the first tubular graft element and the fold region and wherein the second leg is defined between the second end of the first tubular graft element and the fold region;

applying the first tubular graft element over the second section such that the second elongate element extends through the second leg of the first tubular graft element and out of the second end of the first tubular graft element, and such that the fold region is situated between the first and second legs to define the bifurcation;

forming a trunk portion of the endoprosthesis along the mandrel such that the trunk portion extends along a portion of the first section of the mandrel, the trunk portion including a tab that extends across the bifurcation of the first tubular graft element; and securing together the trunk portion and the first tubular graft element to form the endoprosthesis, wherein a first cut line is defined about a circumference of the first tubular graft element in a first region between the first and second ends, the first tubular graft element being incised along the first cut line about a portion of less than an entirety of the first cut line define a first incised portion and a first unincised portion, and the first tubular graft element is folded along the first unincised portion to define the fold region.

14. A method of manufacturing an endoprosthesis that includes a first leg, a second leg, and a bifurcation, the method comprising:

providing a mandrel having a first section and a second section, the second section including a first elongate element and a second elongate element;

providing a first tubular graft element having a first end and a second end;

folding the first tubular graft element to define a fold region, wherein the first leg is defined between the first end of the first tubular graft element and the fold region and wherein the second leg is defined between the second end of the first tubular graft element and the fold region;

applying the first tubular graft element over the second section such that the second elongate element extends through the second leg of the first tubular graft element and out of the second end of the first tubular graft element, and such that the fold region is situated between the first and second legs to define the bifurcation;

forming a trunk portion of the endoprosthesis along the mandrel such that the trunk portion extends along a portion of the first section of the mandrel, the trunk portion including a tab that extends across the bifurcation of the first tubular graft element; and securing together the trunk portion and the first tubular graft element to form the endoprosthesis, wherein a first cut line is defined about a circumference of the first tubular graft element in a first region between the first and second ends, the first tubular graft element being incised along the first cut line about a portion of less than an entirety of the first cut line define a first incised portion and a first unincised portion, a second cut line is defined about the circumference of the first tubular graft element in a second region between the first and second ends that is longitudinally offset from the first region, the first tubular graft element being incised along the second cut line about a portion of less than an entirety of the second cut line to define a second incised portion and a second unincised portion, and a third cut line extends between the first and second cut lines, the first tubular graft element being incised along the third cut line.

15. The method of claim 14, further comprising folding the first tubular graft element along the second unincised portion, the fold region including the folded first unincised portion and the folded second unincised portion.

16. The method of claim 14, wherein the first tubular graft element is applied over the second section such that the fold region extends between the first and second legs to define the bifurcation.

17. The method of claim 14, wherein an excess section is defined in a region bound between the first and second cut lines, and wherein the third cut line bisects the excess section, and wherein the first tubular graft element is applied over the second section such that at least a portion of the excess section extends along the first section of the mandrel away from the bifurcation.

18. The method of claim 17, wherein the portion of the excess section that extends along the first section of the mandrel includes a first flap and a second flap opposite the first flap, wherein free ends of each of the first and second flaps are defined by the third cut line.

19. A method of constructing a multi-lumen graft device having a main graft body and at least two graft legs, the method comprising:

providing a mandrel with a main mandrel body and at least two mandrel legs;

applying over the mandrel a single tubular structure that overlays each of the two mandrel legs and includes at least one tab that overlaps at least a portion of the main mandrel body;

forming the main graft body over the main mandrel body, the main graft body bonded to the at least one tab and positioned to overlap at least a portion of both of the two graft legs; and forming the two graft legs by partially cutting and folding the single tubular structure, with an uncut portion of the single tubular structure extending therebetween, the at least one tab extending away from the uncut portion such that the at least one tab lays against a section of the mandrel.

20. The method of claim 19, wherein at least one stent element is attached to the graft device.

21. The method of claim 19, wherein the single tubular structure includes at least two tabs, each tab being bonded to the main graft body.

22. The method of claim 19, wherein the main mandrel body includes at least one flat taper towards the two mandrel legs, the flat taper defining a transition between the main mandrel body and the mandrel legs.

23. The method of claim 22, wherein the at least one tab is aligned over the flat taper during construction.

* * * * *